United States Patent [19]

Yoshida

[11] 4,403,858
[45] Sep. 13, 1983

[54] DEFECT INSPECTION SYSTEM

[75] Inventor: Hajime Yoshida, Tokyo, Japan

[73] Assignee: Hajime Industries Ltd., Tokyo, Japan

[21] Appl. No.: 236,229

[22] Filed: Feb. 20, 1981

[30] Foreign Application Priority Data

Feb. 21, 1980 [JP] Japan .................................. 55-20965

[51] Int. Cl.³ ............................................ G01N 21/00
[52] U.S. Cl. .................................... 356/237; 356/240; 250/223 B
[58] Field of Search ............... 356/237, 390, 427, 238, 356/239, 240; 250/223 B, 572; 358/106

[56] References Cited

U.S. PATENT DOCUMENTS 4,025,201 5/1977 Deane ................................ 358/106

Primary Examiner—Vincent P. McGraw
Assistant Examiner—L. Dietert
Attorney, Agent, or Firm—Murray Schaffer

[57] ABSTRACT

A defect inspection system in which a reflector body is arranged at such an angle relative to an object to be inspected that in spite of any parallel movements of the image does not overlap the inspected object. The inspected object and the image thereof are both simultaneously picked up by the same television camera. Then, the video signal from the television camera is fed to a processor which then inspects whether or not the object to be inspected contains defects or flaws.

6 Claims, 7 Drawing Figures

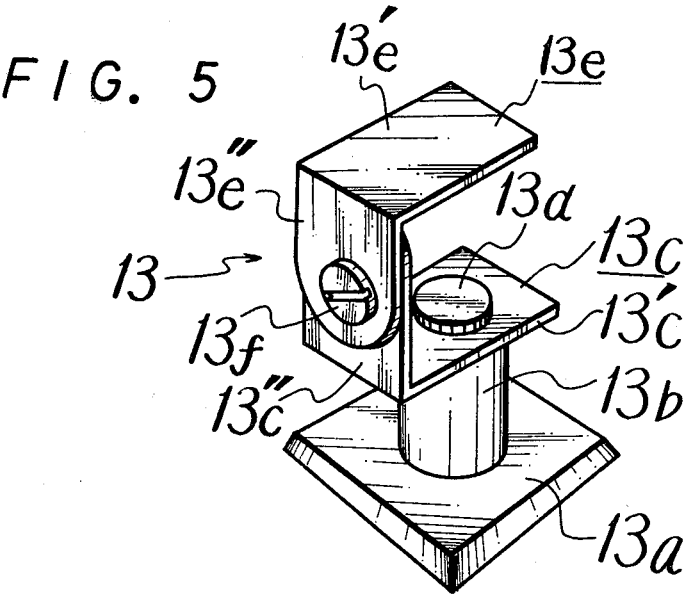
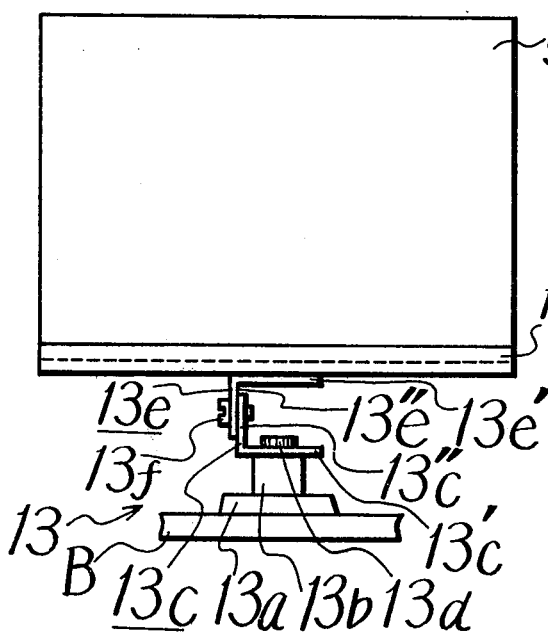
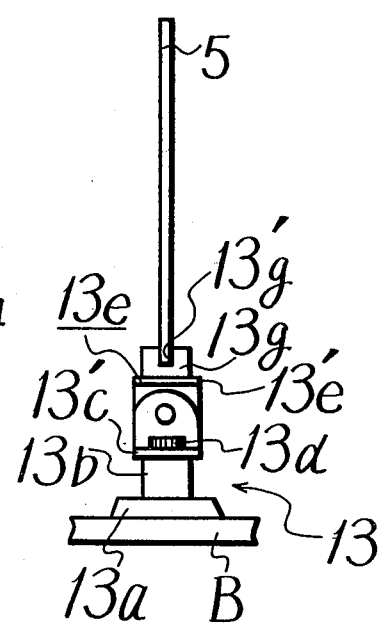

DEFECT INSPECTION SYSTEM

BACKGROUND OF THE INVENTION

1. Field of the Invention

The present invention relates generally to defect inspection systems, and specifically to such defect inspection systems that utilize a television camera.

2. Description of the Prior Art

In the prior art defect inspection systems that utilize television cameras or the like, there is an inevitable, non-detectable or inspectable fault due to the characteristics of the television camera. Such conventional examples of the prior art will be hereunder explained with reference with FIG. 1 and FIG. 2.

FIG. 1 and FIG. 2 illustrate top plan views respectively of objects the defects of which are to be inspected. In the Figures, symbols S and S' generally indicate objects to be inspected. The inspected objects S in FIG. 1 contains a linear flaw or defect 1 or the like which runs at right angles to the scanning direction a of a television camera (although not shown in the drawing) which is used to pick-up the inspected object S. The inspected object S' in FIG. 2 contains a linear flaw or defect 2 or the like, which extends generally in a parallel direction with the scanning direction a of the television camera. In inspecting either of the defects 1 or 2 by the television camera, the scanning direction of the television camera is in the direction as shown by arrow a in FIG. 1 and FIG. 2. In the case of defect 1 on the inspected object S in FIG. 1, since the defect substantially crosses the scanning direction a of the television at the right angles, in the course of the television camera output, such defect 1 is easily detected by creating an irregular level at such portion corresponding to defect 1, or by the reproduction of the defect 1 on a monitor television receiver (not shown). However, since the defect 2 of the inspected object S' as shown on FIG. 2 extends in approximate parallel direction with the television camera scanning direction a, in many cases it may not be scanned by the electron beam of the television camera and accordingly appears to be extremely difficult to be detected.

It is apparent that in the real world, the defects on inspected objects be multifarious (i.e. millions) so that defects of linear nature such as defect 2 in FIG. 2 quite often exist. In other words, there are many cases that linear natured defects that extend in a parallel direction to the television camera scanning direction a do exist. In view of such actual status, the conventional systems contain a serious fault wherein in many cases such defects cannot be detected.

OBJECTS AND SUMMARY OF THE INVENTION

Therefore, a main object of the present invention is to offer a defect inspection system which can positively detect or inspect defects of any shape or in any direction.

The features of the present invention lie in an arrangement of a reflection body such as a mirror or the like, in relation with an inspected object at an angle so that the image of the inspected object will not overlap with the inspected object in spite of any parallel movements, and thereby catching both of the inspected object and its image on the reflector body by the same television camera equally.

According to an aspect of the present invention, a defect inspection system is provided which comprises:
(a) an image sensing means for picking up an object to be inspected;
(b) means for providing an optical image of said object; said optical image providing means so located that the optical image of said object provided thereby is not in parallel to said object, said image sensing means being so located that both said object and said optical image thereof are picked up thereby; and p0
(c) means for receiving an output from said image sensing means and inspecting whether or not said object contains flaws.

The other objects, features and advantages of the present invention will become apparent from the following description taken in conjunction with the drawings attached.

BRIEF DESCRIPTION OF THE DRAWINGS

FIG. 5 is a perspective view of a mounting device for a reflector shown in FIG. 4;

FIG. 6 is a front view of the reflector supported by the mounting device shown in FIGS. 4 and 5;

FIG. 7 is the side view of FIG. 6.

DESCRIPTION OF THE PREFERRED EMBODIMENTS

Figure 1:
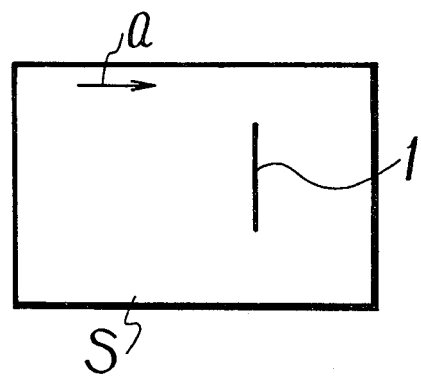
FIG. 1 and FIG. 2 are respectively schematic diagrams that illustrate top plan views of objects to be inspected.
Figure 2:
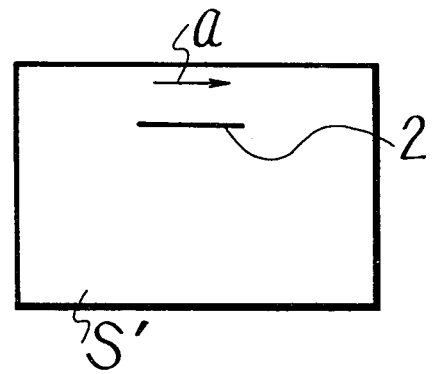
Figure 3:
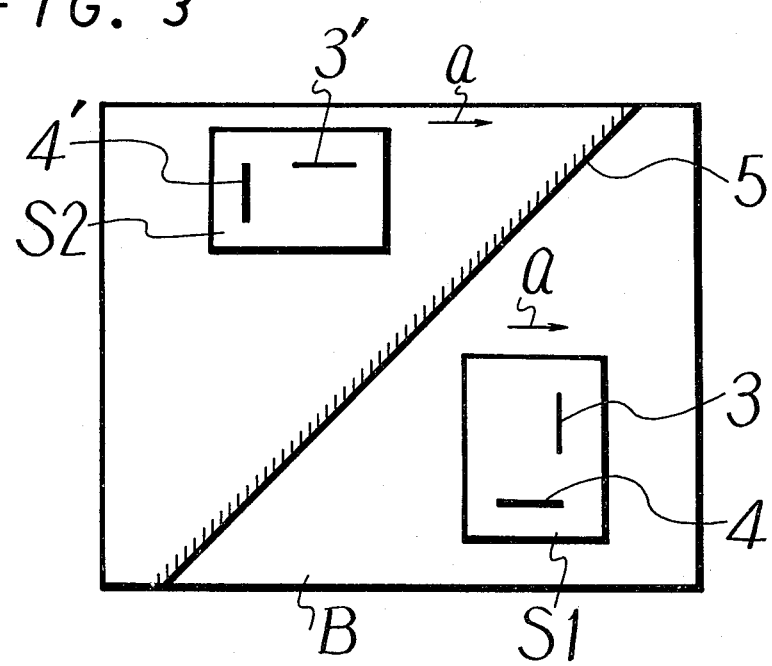
FIG. 3 is a schematic drawing explaining one example of the present inspection.

One example of the present invention will be described in reference with FIG. 3. In FIG. 3, S1 is an object to be inspected located on an inspection platform B which contains a defect 3 which runs about at the right angle to the scanning direction a of a television camera which is not shown in the drawing, and a flaw 4 which runs approximately in parallel to the scanning direction a of the same camera.

In the present invention, a reflection body such as a mirror or the like 5 is arranged on the inspection platform B in such a manner that the image of the inspected object S1, which is indicated as symbol S2 on the drawing in relation to the inspected object S1, does not overlap on the object S1 in spite of any parallel movement. In the example of FIG. 3, the angle of the mirror 5 relative to the inspected object S1 is arranged so that images 3' and 4' on the inspected object image S2 on mirror 5 appear at an approximate right angle to the defects 3 and 4 on the inspected object S1.

Then, although the television camera is not indicated on FIG. 3, the television camera is arranged so that both of the inspected object S1 and its image S2 are picked up by the television camera in their state as illustrated on FIG. 3 and displayed on its pick-up screen. By such arrangement, the pick-up screen on the television camera or on the monitor television receiver screen (not indicated on FIG. 3 displays), the inspected object S1 and the image S2 in the relation as illustrated on FIG. 3. Therefore, the defect 3 on the inspected object S1 which runs at an approximate right angle to the scanning direction a of the television camera can be easily detected or inspected as was with the conventional cases. On the other hand, the parallel defect 4 on the inspected object S1 to the scanning direction a of the television camera, is not detected as it is, but the defect 4' on the image S2 on mirror 5 is in approximate right angle to the scanning direction a (the image is arranged to show an approximate right angle to the scanning direction a as above described) so that it appears in a right angle similar to defect 3 against the scanning direction a which now can be easily detected or inspected. In other words, defect 4 on the inspected object S1 which extends approximately in parallel to the scanning direction a of the television camera, would appear to be difficult to detect or inspect as it is, but in the image S2 on the mirror 5 is easily detected since it appears as defect 4' extending in approximate right angle to the scanning direction a of the television camera Such defect 4' is also included in the pick-up screen of the same television camera, while it can be easily detected or inspected.

As above described, according to the present invention, any defects can be positively inspected by an extremely simple construction.

Figure 4:
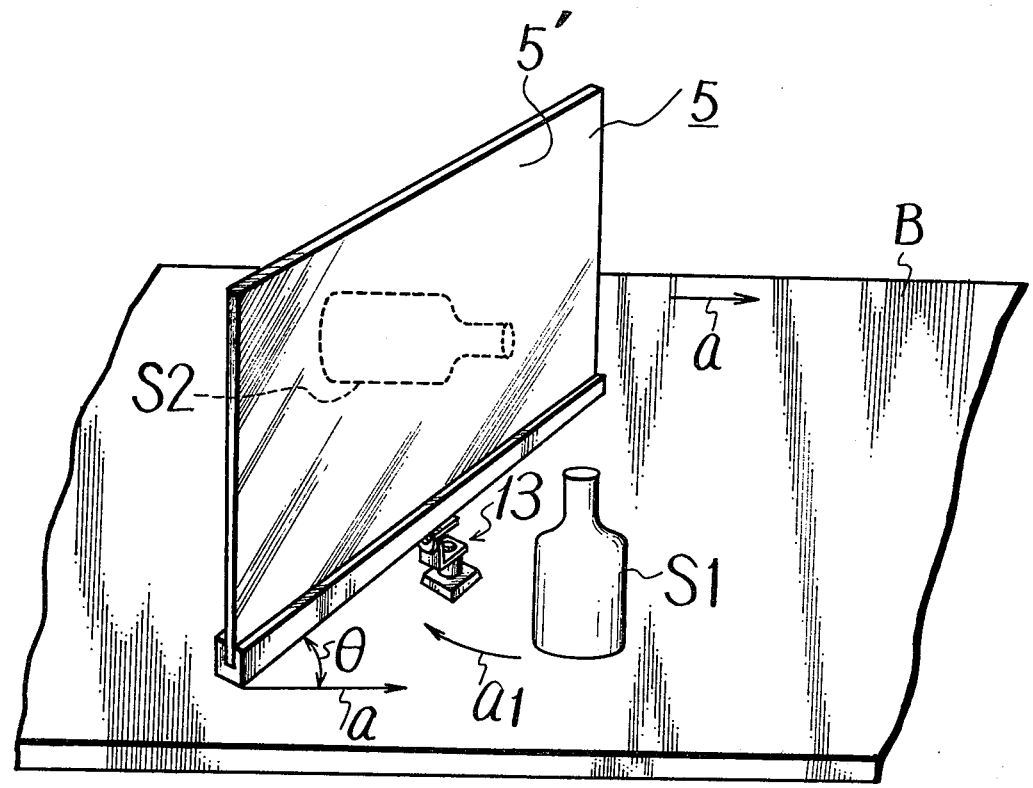
FIG. 4 is a perspective view showing an embodiment of the present invention.
Figure 4:
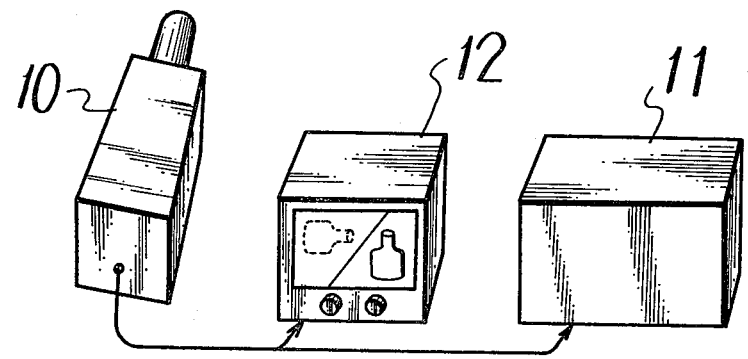

Turning to FIG. 4, the present invention will be practically explained. In FIG. 4, 10 designates a television camera, 11 a defect or flaw detecting section such as a computer (processor), and 12 a monitor television receiver, respectively.

In the example of the invention, the object S1 which defect or flaw is to be inspected is, for example, a bottle and located on the inspection platform B. The reflector 5 such as a mirror is positioned on the platform B, through a suitable mounting device 13, which will be described later, at such a location that the mirror is tilted to the plane of the platform B, by about 45°, the image S2 of the bottle S1 produced in the mirror 5 is rotated about 90° in the direction indicated by an arrow a1 (in FIG. 4 in the clockwise direction from vertical to horizontal) from the bottle S1 itself. Thus, the positional relation of the object or bottle S1 to its image S2 by the mirror 5 is substantially same as that shown in FIG. 3.

In FIG. 4, for the sake of further illustration, the mirror 5 is also located such that when its mirror surface 5' is considered substantially perpendicular to the surface of the inspection platform B, it makes an angle θ with the scanning direction a. When angle θ is chosen at about 45°, the object S1 and its image S2 will appear in same vertical plane parallel to the direction of scanning a. By selecting the angles as illustrated, the camera 10 will be able to view simultaneously both the object S1 and the image S2 in different relative directions. In fact, however, it is possible that the mirror 5 may be located with angles of its mirror surface 5' to the surface of the platform B and to the scanning direction a, different from the above within the range that both of the object S1 and its mirror image S2 are simultaneously picked up by the same television camera 10.

Upon inspecting the object or bottle S1, the television camera 10 is so located that it scans both the bottle S1 itself and its image S2 provided by the mirror 5 and generates a video signal thereof. The video signal delivered from television camera 10 is supplied to the flaw detecting section such as processor 11 in which it is inspected whether or not the bottle S1 contains defects or flaws, as in the well known manner.

Further, if desired, the video signal from television camera 10 is also supplied to monitor television receiver 12 to be reproduced as images on its picture screen as shown in FIG. 4. Thus, the bottle S1 may be visually inspected.

Turning to FIG. 5 which is a perspective view of the main part of the mounting device 13 for the mirror, and FIG. 6 which is the front view of mirror 5 supported by the mounting device 13 and FIG. 7 which is the side view of FIG. 6, an example of the mounting device 13 according to the invention will be now described.

As shown, especially in FIG. 5, this example of the mounting device 13 is a kind of a so-called universal joint. In the figures, reference 13a designates a stand or base which is placed on the surface of platform B on which surface the bottle S1 to be inspected is located. A post 13b is fixedly planted on the base 13a to stand in the vertical direction. An L-shaped plate 13c is rotatably attached by its horizontal arm 13c' to the top of post 13b by means of a bolt 13d so that the arm 13c' of L-shaped plate 13c becomes horizontal or parallel to the surface of platform B and its vertical arm 13c" is vertical or perpendicular to the surface of platform B. An inversed L-shaped plate 13e is fixedly coupled at its vertical arm 13e" to that 13c" of L-shaped arm 13c by means of a screw 13f so that the horizontal arm 13e' of inverse L-shaped plate 13e becomes parallel to the horizontal arm 13c' of L-shaped plate 13c and hence to the surface of platform B. A supporting member 13g of a bar-shape provided with a groove 13g' along all over the lengthwise direction thereof, into which groove 13g' the mirror 5 is engaged to be fixedly supported thereby, is fixed on the horizontal arm 13c' of inverse L-shaped plate 13e so that the supporting member 13g and hence the groove 13g' lies in parallel to the surface of the platform B. Thus, an example of the mounting device 13 or the mirror 5 according to the invention as shown in FIG. 4 is formed.

With the mounting device 13 for the mirror 5 according to the invention, if the bolt 13d is somewhat loosened and the plate 13c is rotated in the horizontal plane about the bolt 13d, the angle θ of mirror 5 to the scanning line a can be varied as desired, while if the screw 13f is loosened and the plate 13e is rotated about the screw 13f relative to the other plate 13c within the plane perpendicular to the surface of platform B, the angle of mirror 5 to the surface of platform B can be varied. That is, the angles of mirror 5 relative to both of scanning direction a and the surface of platform B can be adjusted as desired by operating the mounting device 13. In other words, the position of image S2 of object S1 by the mirror 5 relative to the latter can be varied by adjusting the mounting device 13.

It is needless to mention that, while in the example as illustrated on FIG. 3 and FIG. 4, the mirror 5 is arranged in a manner so that the image S2 of the inspected object S1 is rotated for about 90 degrees, the placement of the mirror 5 need not be confined to the case of this example, but in essence, the mirror 5 may be placed in relation to the inspected object S1, so that the defect 4 on inspected object S1 which is parallel to the scanning direction a of television camera, will appear to extend at a crossing angle to the scanning direction a on image S2 on the mirror 5. In other words, the angle of the placement of mirror 5 in relation to the inspected object S1, can be of any tilted angle against the inspected object S1 as long as it is other than parallel. Of course, it is necessary that both of the inspected object S1 as well as the image S2 of the same on mirror 5 be picked at the same time by the single television camera.

It is also obvious that the above illustration is one preferred example of the present invention and that any one skilled in the art may make many modifications or changes without escaping the spirit of the novel concepts of the present invention.

I claim as my invention:

1. A defect inspection system comprising:
   (a) an image sensing means for picking up an object to be inspected;
   (b) means for providing an image of said object; said image providing means being so located that the image of said object provided thereby is not in parallel to said object, said image sensing means being so located that both of said object and said image thereof are picked up thereby; and
   (c) means for receiving an output from said image sensing means and inspecting whether or not said object contains flaws.

2. A defect inspection system according to claim 1 further comprising a monitoring means which receives the output from said image sensing means and reproduces thereon said object and said image thereof.

3. A defect inspection system as claimed in claim 1, wherein said image providing means is a reflector.

4. A defect inspection system according to claim 1 further comprising means for supporting said image providing means.

5. A defect inspection system as claimed in claim 4, wherein said supporting means includes means for changing the angle of said image providing means relative to said object.

6. A defect inspection system according to claim 3, including supporting means for said reflector comprises a universal mounting enabling said reflector to be tilted at an angle to the horizontal and rotated about a vertical axis.

* * * * *